(12) United States Patent
Lee

(10) Patent No.: US 9,820,830 B2
(45) Date of Patent: Nov. 21, 2017

(54) ORTHOPEDIC APPLIANCE FOR TEMPOROMANDIBULAR JOINT

(71) Applicant: Sung-wan Lee, Changwon-si (KR)

(72) Inventor: Sung-wan Lee, Changwon-si (KR)

(73) Assignee: HI-FEEL WORLD CO., LTD (KR)

( * ) Notice: Subject to any disclaimer, the term of this patent is extended or adjusted under 35 U.S.C. 154(b) by 0 days.

(21) Appl. No.: 14/743,276

(22) Filed: Jun. 18, 2015

(65) Prior Publication Data

US 2015/0282900 A1    Oct. 8, 2015

Related U.S. Application Data

(63) Continuation of application No. PCT/KR2014/010843, filed on Nov. 12, 2014.

(30) Foreign Application Priority Data

Nov. 12, 2013  (KR) .................. 10-2013-0136611

(51) Int. Cl.
*A61C 7/36*        (2006.01)
*A61C 7/08*        (2006.01)

(52) U.S. Cl.
CPC . *A61C 7/36* (2013.01); *A61C 7/08* (2013.01)

(58) Field of Classification Search
CPC .. A61C 7/36; A61C 7/08; A61F 5/566; A61B 17/663
USPC ............... 433/6, 7, 18–19, 24; 128/848, 859
See application file for complete search history.

(56) References Cited

U.S. PATENT DOCUMENTS

| 6,012,920 A * | 1/2000 | Woo .................. A61C 7/10 433/19 |
| 6,526,982 B1 * | 3/2003 | Strong ............... A61F 5/566 128/848 |
| 8,932,054 B1 * | 1/2015 | Rosenberg ........... A61C 7/36 433/19 |

(Continued)

FOREIGN PATENT DOCUMENTS

| JP | 10-508762 A | 9/1998 |
| KR | 10-2012-0033386 A | 4/2012 |

(Continued)

OTHER PUBLICATIONS

WIPO, International Search Report (PCT/KR2014/010843), dated Jan. 27, 2015.

*Primary Examiner* — Tammie K Heller

(74) *Attorney, Agent, or Firm* — Park & Associates IP Law, P.C.

(57) ABSTRACT

An orthopedic appliance for a temporomandibular joint, includes: an upper teeth supporter and a lower teeth supporter, each of which includes a front arch portion corresponding to front teeth, and a pair of rear legs extended from the front arch portion, facing with each other and corresponding to a molar region; at least one set of upper and lower pivots which are respectively coupled to the upper teeth supporter and the lower teeth supporter and rotatable in at least one direction among forward, backward, leftward and rightward directions; and a connection member which connects the upper pivot and the lower pivot and adjusts a space between the upper pivot and the lower pivot. Thus, it is easy to adjust relative movement in a horizontal direction and height between the upper and lower teeth supporters.

8 Claims, 8 Drawing Sheets

(56) References Cited

U.S. PATENT DOCUMENTS

2007/0224567 A1\* 9/2007 Robson .................. A61F 5/566
 433/6
2014/0342299 A1 11/2014 Jung

FOREIGN PATENT DOCUMENTS

| KR | 20-2013-0005255 U | 9/2013 |
| KR | 10-1344394 B1 | 12/2013 |
| KR | 10-1352200 B1 | 1/2014 |
| WO | 95/14449 A1 | 6/1995 |

\* cited by examiner

ORTHOPEDIC APPLIANCE FOR TEMPOROMANDIBULAR JOINT

REFERENCE TO RELATED APPLICATIONS

This is a continuation of pending International Patent Application PCT/KR2014/010843 filed on Nov. 12, 2014, which designates the United States and claims priority of Korean Patent Application No. 10-2013-0136611 filed on Nov. 12, 2013, the entire contents of which are incorporated herein by reference.

FIELD OF THE INVENTION

Apparatuses consistent with the exemplary embodiments relate to an orthopedic appliance for a temporomandibular joint.

BACKGROUND OF THE INVENTION

Malocclusion refers to a defect in a normal position between upper teeth and lower teeth, thereby making an aesthetic and functional problem. Such malocclusion is mostly found when the upper and lower parts of a temporomandibular joint are dislocated to each other. Therefore, an orthodontic treatment is needed for correcting this dislocation.

Conventionally, an individual teeth supporter has been manufactured and mounted to correct the position of the temporomandibular joint. It is impossible for such a conventional supporter to gradually respond to a malocclusion condition change of a patient. Accordingly, there has been proposed a teeth supporter that can be gradually and minutely adjusted in response to the change in a patient's malocclusion condition. However, there has been no substantive effect since this minutely adjustable teeth supporter is also virtually impossible to make relative movement in a horizontal direction between its upper and lower teeth supporters.

SUMMARY OF THE INVENTION

An aspect of one or more exemplary embodiments may provide an orthopedic appliance for a temporomandibular joint, in which the relative horizontal movement and height adjustment between upper and lower teeth supporters are easy.

In accordance with an embodiment, there is provided an orthopedic appliance for a temporomandibular joint, including: an upper teeth supporter and a lower teeth supporter, each of which includes a front arch portion corresponding to front teeth, and a pair of rear legs extended from the front arch portion, facing with each other and corresponding to a molar region; at least one set of upper and lower pivots which are respectively coupled to the upper teeth supporter and the lower teeth supporter and rotatable in at least one direction among forward, backward, leftward and rightward directions; and a connection member which connects the upper pivot and the lower pivot and adjusts a space between the upper pivot and the lower pivot, wherein the connection member includes an adjustment screw in at least one end portion thereof, and at least one of the upper pivot and the lower pivot includes an engagement screw corresponding to the adjustment screw.

The upper pivot and the lower pivot may be installed in the rear leg and correspond to each other.

The upper pivot and the lower pivot may have spherical surfaces, and the upper and lower teeth supporters may respectively include pivot accommodating portions having spherical surfaces corresponding to the spherical surfaces of the pivots and accommodating the pivots to be rotatable.

The adjustment screws may be respectively male-threaded in opposite end portions of the connection member and spiraled in opposite directions to each other, and the engagement screws may be respectively female-threaded in the upper pivot and the lower pivot and spiraled in opposite directions to each other corresponding to the adjustment screws.

At least one opposite end of the connection member may include a driver groove for rotation control, the engagement screw may be formed by penetration for insertion of a screw driver, at least one of the upper pivot and the lower pivot may include a stop projection for stopping rotation of the engagement screw with regard to an axial line, the rear leg may include a stopper to engage with the stop projection and stop the rotation of the engagement screw with regard to the axial line, and the connection member may include a rotary knob in a middle region thereof for rotation control.

BRIEF DESCRIPTION OF THE DRAWINGS

The above and/or other aspects will become apparent and more readily appreciated from the following description of exemplary embodiments, taken in conjunction with the accompanying drawings, in which.

DETAILED DESCRIPTION OF THE INVENTION

Hereinafter, exemplary embodiments will be described with reference to accompanying drawings.

Figure 1:
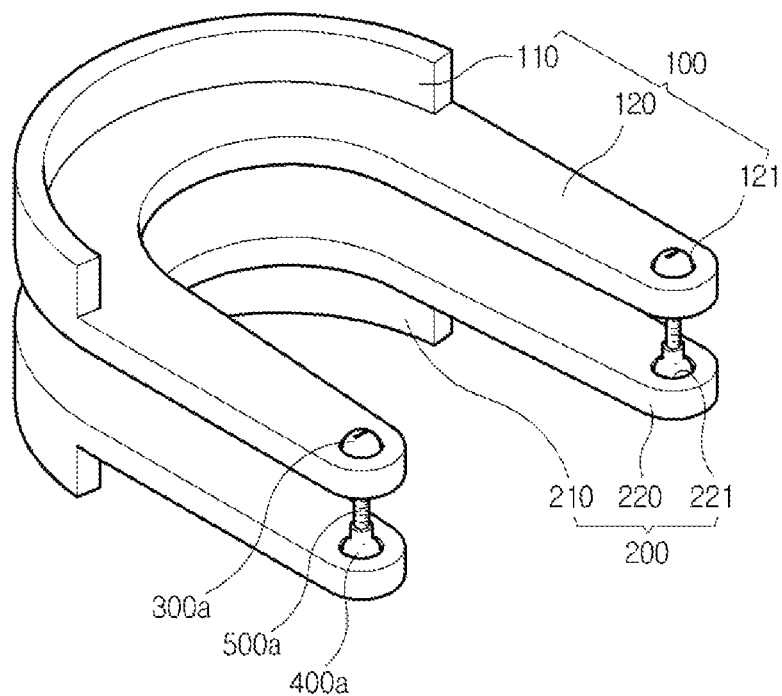
FIG. 1 is a perspective view of an orthopedic appliance for a temporomandibular joint according to an exemplary embodiment.

As shown in FIG. 1, an orthopedic appliance for a temporomandibular joint includes an upper teeth supporter 100 and a lower teeth supporter 200, upper pivots 300a and lower pivots 400a respectively coupled to the upper teeth supporter 100 and the lower teeth supporter 200, and connection members 500a connecting the upper pivot 300a and the lower pivot 400a.

The upper teeth supporter 100 is formed with a front arch portion 110 corresponding to front teeth. The front arch portion 110 includes a flange extended and protruding in an upper direction from a horizontal base portion, thereby supporting the front teeth. Further, a pair of opposing rear legs 120 are coupled to and extended from the front arch portion 110 and correspond to a molar region.

Like the upper teeth supporter 100, the lower teeth supporter 200 facing the upper teeth supporter 100 is formed with a front arch portion 210. The front arch portion 210 includes a flange extended and protruding in a lower direction from a horizontal base portion, thereby supporting the front teeth. Further, a pair of opposing rear legs 220 are coupled to and extended from the front arch portion 210 and correspond to the molar region.

The rear legs 120 and 220 respectively couple with the upper pivot 300a and the lower pivot 400a. The upper pivot 300a and the lower pivot 400a are rotatable in all directions, i.e. forward, backward, leftward and rightward. Alternatively, the upper pivot 300a and the lower pivot 400a may be rotatable in only forward and backward direction or only leftward and rightward direction.

As necessary, the upper teeth supporter 100 and the lower teeth supporter 200 may be formed by double-shot injection molding to have them covered with a material, such as silicon or the like, which is softer than the teeth supporters 100 and 200. If the teeth supporters 100 and 200 are covered with the soft material, the teeth supporters 100 and 200 may closely contact and firmly hold the teeth. The soft material may be molded to cover the whole or a part of the teeth supporters 100 and 200.

Further, the upper teeth supporter 100 and the lower teeth supporter 200 may be manufactured in the form of a wire. If the upper teeth supporter 100 and the lower teeth supporter 200 are made of wires, the wires are formed to have an arch shape to secure to the front teeth, and their rear portions are coupled to the upper pivot 300a and the lower pivot 400a in the same manner as the above-described rear legs 120 and 220.

Figure 2:
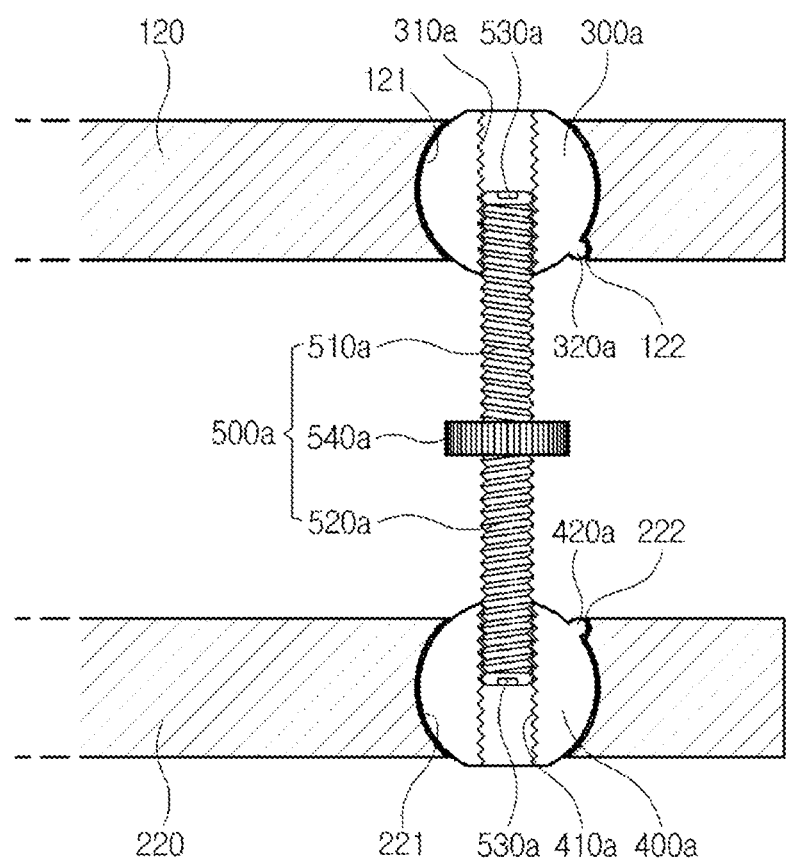
FIG. 2 is a cross-section view of a pivot and a connection member.

As shown in FIG. 2, the surfaces of the upper pivot 300a and the lower pivot 400a have a spherical shape. The rear legs 120 and 220 respectively include pivot accommodating portions 121 and 221 that have a spherical groove surface corresponding to the shape of the pivots 300a and 400a.

In addition, the connection member 500a connects the upper pivot 300a and the lower pivot 400a and adjusts a space between the upper pivot 300a and the lower pivot 400a. The connection member 500a includes adjustment screws 510a and 520a formed as a male-threaded screw, and the upper pivot 300a and the lower pivot 400a respectively include engagement screws 310a and 410a formed as a female-threaded screw and corresponding to the adjustment screws 510a and 520a. The adjustment screws 510a and 520a are spiraled in opposite directions at positions to which the upper pivot 300a and the lower pivot 400a are respectively coupled, and the engagement screws 310a and 410a are also formed corresponding to the adjustment screws 510a and 520a. Since the adjustment screws 510a and 520a are spiraled in the opposite directions to each other, the upper pivot 300a and the lower pivot 400a get closer to or further away from each other as the connection member 500a is rotated. In other words, when the connection member 500a is rotated, the upper pivot 300a moves downward in the connection member 500a but the lower pivot 400a coupled to the connection member 500a spiraled in the opposite direction moves upward in the connection member 500a. Thus, the upper pivot 300a and the lower pivot 400a get closer to each other. On the contrary, if the connection member 500a is rotated in the opposite direction to the foregoing direction, the upper pivot 300a moves upward and the lower pivot 400a moves downward so that they can get further away from each other.

To facilitate the rotation of the connection member 500a, a driver groove 530a is formed on the top of the adjustment screw 510a. When a screw driver is put in the driver groove 530a and then rotated, the connection member 500a rotates with regard to an axial line so that a space between the upper pivot 300a and the lower pivot 400a can be adjusted. As necessary, the driver groove 530a may be formed on the bottom of the adjustment screw 520a. Alternatively, driver grooves may be formed on both ends of the connection member 500a so that a user can select the driver groove as desired by him/her to rotate the connection member 500a. The adjustment screws 510a and 520a respectively penetrate and thus jut out from the upper pivot 300a and the lower pivot 400a so that the screw driver can be easily put in the driver groove 530a.

In addition, a rotary knob 540a is provided in a middle region of the connection member 500a so as to facilitate the rotation of the connection member 500a. Through the rotary knob 540a, a user can rotate the connection member 500a by hand without any separate screw driver.

The upper pivot 300a and the lower pivot 400a respectively have stop projections 320a and 420a to be at a standstill when the adjustment screws 510a and 520a are rotated with respect to the axial line. In addition, the rear legs 120 and 220 respectively have stoppers 122 and 222 to engage with the stop projections 320a and 420a and stop the rotation of the upper and lower pivots 300a and 400a with respect to the axial line of the adjustment screws 510a and 520a. The stop projections 320a and 420a are forcibly fitted to the stoppers 122 and 222, respectively. As necessary, if the space between the upper teeth supporter 100 and the lower teeth supporter 200 is adjusted by rotating not the connection member 500a but the pivots 300a and 400a, the stop projections 320a and 420a and the stoppers 122 and 222 are not needed.

Figure 3A:
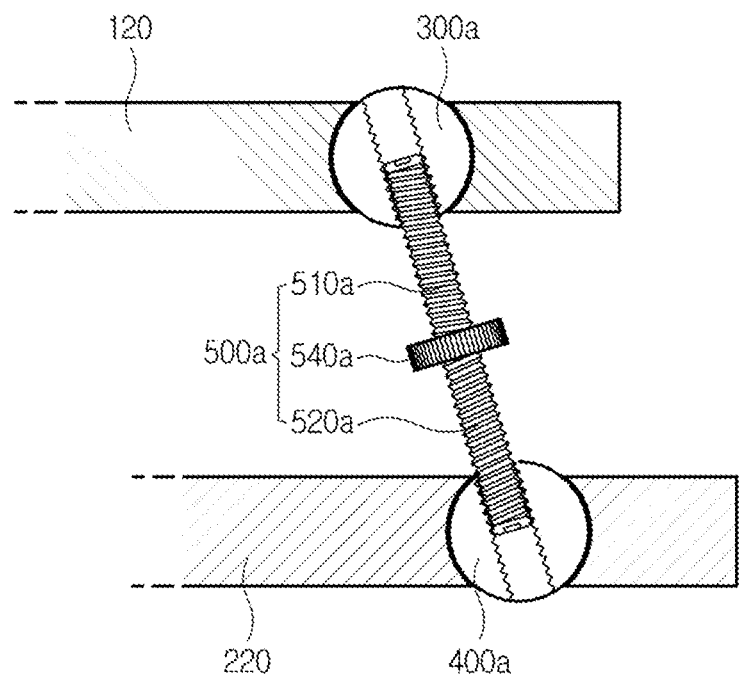
FIG. 3A and FIG. 3B are cross-section views of the pivot and the connection member in accordance with relative horizontal movement between teeth supporters.

With this configuration, the adjustment process of the orthopedic appliance for the temporomandibular joint according to an exemplary embodiment will be described with reference to FIG. 3. FIG. 3A shows that the upper teeth supporter 100 is moved more forward than the lower teeth supporter 200. This corresponds to settings for initial adjustment of a malocclusion patient who has a lower jaw moved more backward than an upper jaw. In this state, if adjustment in inclination and height is needed for the connection member 500a coupled to the upper pivot 300a and the lower pivot 400a, a space in a horizontal direction between the upper teeth supporter 100 and the lower teeth supporter 200 is adjustable by controlling an angle of the connection member 500a since the upper teeth supporter 100 and lower teeth supporter 200 are pivotally coupled.

Figure 3B:
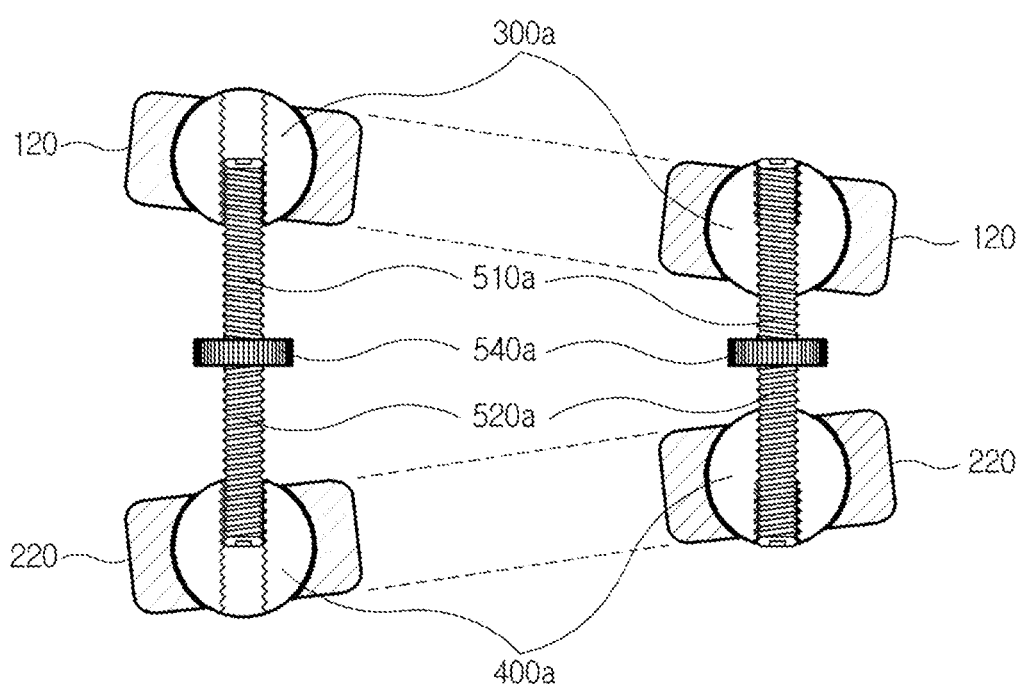

FIG. 3B corresponds to settings for initial adjustment of a malocclusion patient who has a temporomandibular joint different in height between left and right sides, in which height adjustment is achieved by controlling the height of the connection member 500a. For example, the upper pivot 300a and the lower pivot 400a may be spaced apart from each other as shown in the left side of FIG. 3B, or get close to each other as shown in the right side of FIG. 3B through the rotary knob 540a of the connection member 500a, thereby preparing the settings for the jaw of the malocclusion patient.

For stably retaining or adjusting the settings of FIG. 3A or FIG. 3B, a separate retainer or adjuster may be provided at a different region of the upper and lower teeth supporters 100 and 200. The retainer may be given in the form of a block, a clip or the like, and the adjuster may be achieved by a screw or a cam mechanism. Besides, the retainer or the adjuster may have various shapes to be combined and used in this exemplary embodiment.

The foregoing adjustment mechanism according to the exemplary embodiments shown in FIG. 2 and FIG. 3, which includes the upper pivot 300a, the lower pivot 400a and the connection member 500a, is installed in the rear legs 120 and 220 of the upper and lower teeth supporters 100 and 200. However, the same adjustment mechanism may be installed in a different region of the teeth supporters 100 and 200. For example, as shown in FIG. 4 and FIG. 5, accommodating grooves 115 and 215 may be formed to be cut open as much as a predetermined length in the front arch portions 110 and 210 along a height direction so that an upper pivot 300i, a lower pivot 400i and connection members 510i, 520i and 540i can be installed in the accommodating grooves 115 and 215, thereby allowing relative movement in a horizontal direction between the upper and lower teeth supporters 100 and 200 and at the same time correcting opening motion or horizontal dislocation of a jaw by opening or closing the space between the upper and lower teeth supporters 100 and 200.

Figure 4:
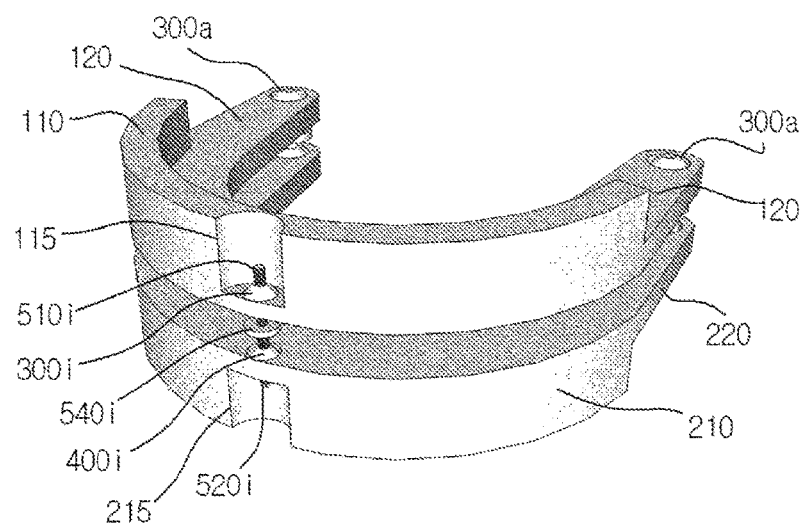
FIG. 4 and FIG. 5 are a perspective view and a front view showing that a pivot and a connection member are additionally installed in a front arch portion.
Figure 5:
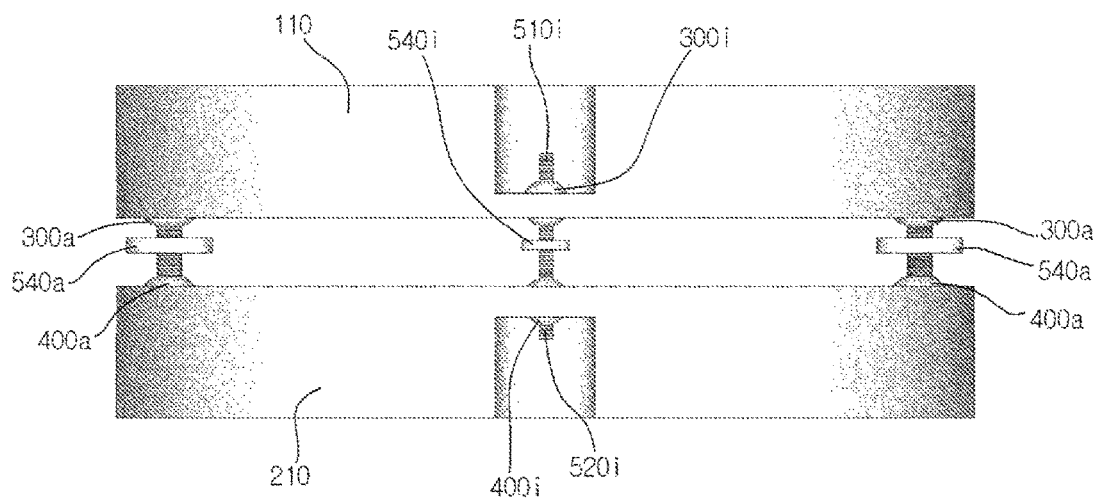
Figure 6:
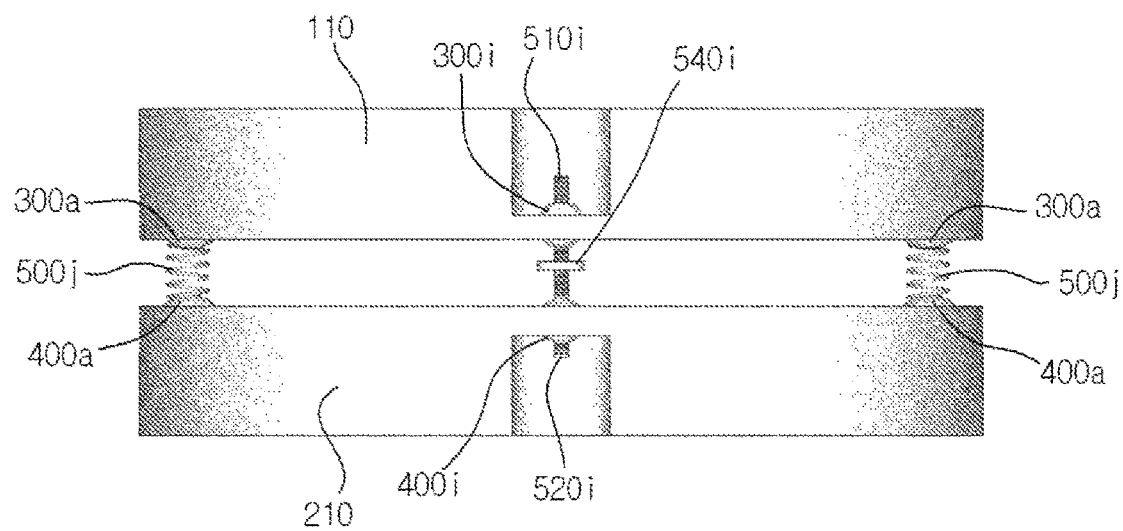
FIG. 6 is a front view showing that a spring is installed as the connection member.

Like this, if the mechanism for height adjustment as shown in FIGS. 4 and 5 is applied to the front arch portions 110 and 120, the connection member 500a of the rear legs 120 and 220 may be provided in the form of a spring as shown in FIG. 6.

The orthopedic appliance for the temporomandibular joint may be manufactured variously like the exemplary embodiments shown in FIG. 7 and FIG. 8.

Figure 7A:
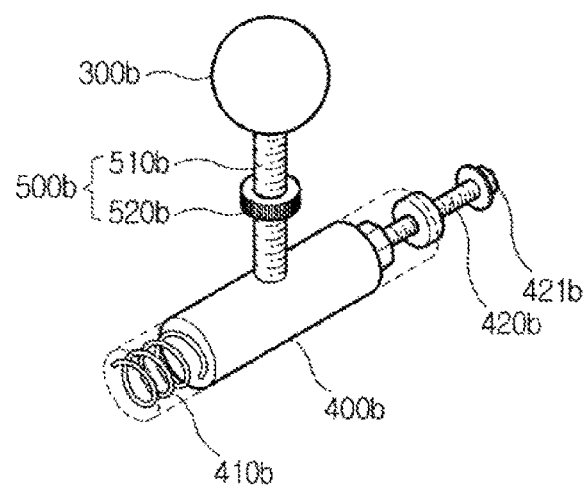
FIGS. 7A to 7C are perspective views of a pivot and a connection member according to another exemplary embodiment.

Referring to FIG. 7A, an upper pivot 300b may have a spherical shape, and a lower pivot 400b may have a cylindrical shape. The upper pivot 300b and the lower pivot 400b are coupled to opposite ends of a connection member 500b including an adjustment screw 510b and a rotary knob 520b. Since the upper pivot 300b is shaped like a sphere, rotation is allowed in all directions, i.e. forward, backward, leftward and rightward directions. The lower pivot 400b is movable forward and backward through screw control using a front spring 410b and a rear bolt 420b, and also rotatable in leftward and rightward. At the end of the bolt 420b, a grip 421b is provided for facilitating the screw control.

Figure 7B:
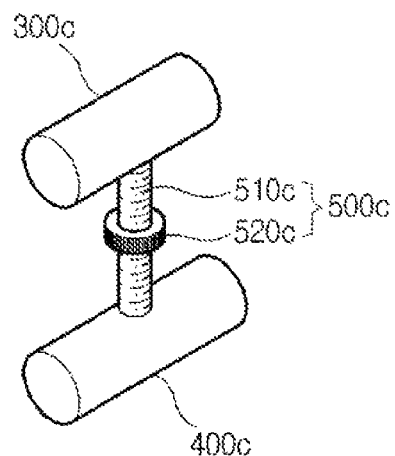

Referring to FIG. 7B, an upper pivot 300c and a lower pivot 400c are all shaped like a cylinder, and arranged in a lengthwise direction of the rear legs 120 and 220 so that the teeth supporters 100 and 200 can be adjustable in leftward and rightward directions. The upper pivot 300c and the lower pivot 400c are coupled to opposite ends of a connection member 500c including an adjustment screw 510c and a rotary knob 520c. The upper pivot 300c and the lower pivot 400c are rotatable with respect to an axial direction, and therefore not the forward and backward adjustment but only the leftward and rightward adjustment is possible. Since the upper and lower teeth supporters 100 and 200 are adjustable in the leftward and rightward directions, this embodiment is applied to patients who need the teeth supporters 100 and 200 fixed in the forward and backward directions and adjustable only in the leftward and rightward directions.

Figure 7C:
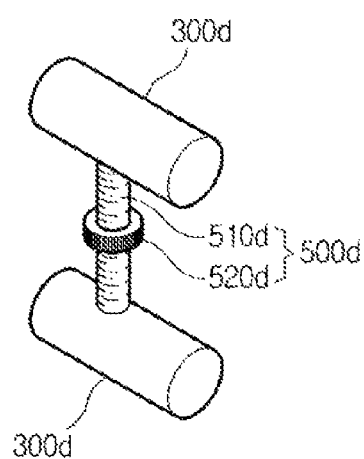

Referring to FIG. 7C, an upper pivot 300d and a lower pivot 400d are all shaped like a cylinder like those of FIG. 7B, arranged in a direction perpendicular to the lengthwise direction of the rear legs 120 and 220, and coupled to opposite ends of a connection member 500d that includes an adjustment screw 510d and a rotary knob 520d. This embodiment is applied to patients who need the teeth supporters 100 and 200 fixed in the leftward and rightward directions and adjustable only in the forward and backward directions.

The upper pivot 300a and the lower pivot 400a, and the connection member connecting them may be varied in shape as shown in FIG. 7.

Figure 8A:
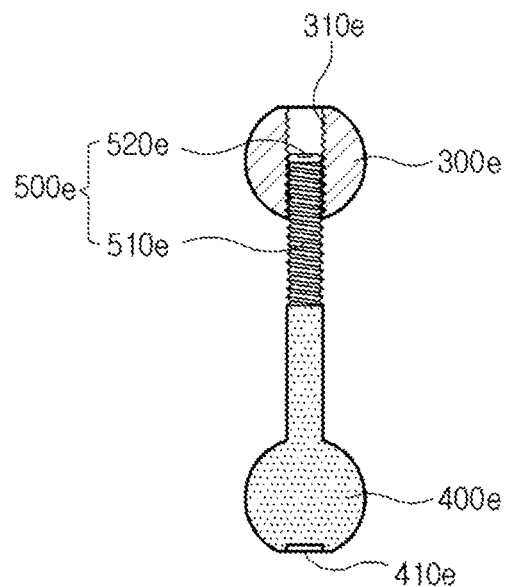
FIGS. 8A to 8D are perspective views of a pivot and a connection member according to still another exemplary embodiment.

Referring to FIG. 8A, an upper pivot 300e is formed with an engagement screw 310e having a female thread, and a region of a connection member 500e corresponding to an engagement screw 310e is formed with an adjustment screw 510e. The connection member 500e is extended downward and formed integrally with a lower pivot 400e. In addition, a driver groove 520e is formed on the top of the adjustment screw 510e. As necessary, a driver groove 410e may be formed on the bottom of the lower pivot 400e. Thus, the space between the upper pivot 300e and the lower pivot 400e is adjustable by rotating a screw driver put in the driver groove 520e on the top of the connection member 500e or the driver groove of the lower pivot 400e with respect to an axial direction.

Figure 8B:
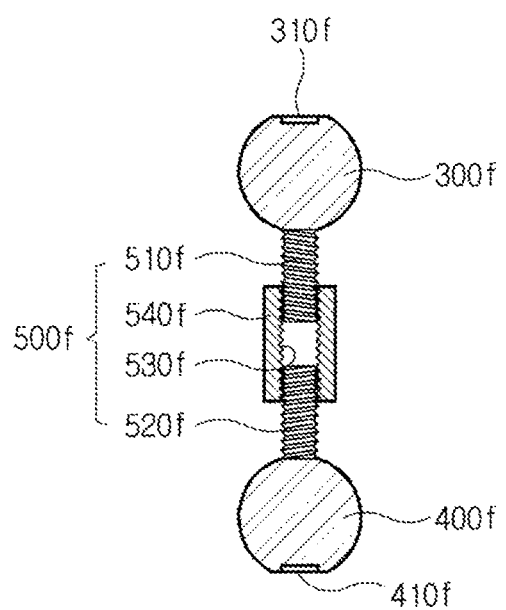

Referring to FIG. 8B, a connection member 500f having adjustment screws 510f and 520f is extended from an upper pivot 300f and a lower pivot 400f. The upper pivot 300f and the lower pivot 400f are formed with driver grooves 310f and 410f at ends thereof, and the adjustment screws 510f and 520f are spiraled in opposite directions to each other. If the upper pivot 300f is rotated with respect to the axial direction through the driver groove 310f of the upper pivot 300f, only the upper pivot 300f is changed in position while the lower pivot 400f disconnected from the upper pivot 300f is not changed in position. Likewise, if the lower pivot 400f is rotated, only the lower pivot 400f is moved. The connection members 500f are connected by a rotary knob 540f having an engagement screw 530f. When the rotary knob 540f is rotated, the upper pivot 300f and the lower pivot 400f get closer to or further away from each other since they are rotated together by the adjustment screws 510f and 520f spiraled in opposite directions to each other.

Figure 8C:
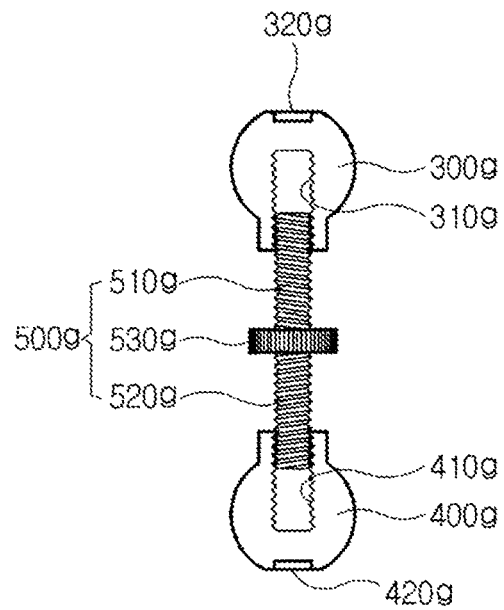

Referring to FIG. 8C, engagement screws 310g and 410g are integrally extended from an upper pivot 300g and a lower pivot 400g, and each of the engagement screws 310g and 410g is connected to a connection member 500g. An upper portion of the connection member 500g has an adjustment screw 510g corresponding to the upper pivot 300g, and a lower portion of the connection member 500g has an adjustment screw 520g corresponding to the lower pivot 400g and spiraled in an opposite direction to the spiral of the adjustment screw 510g of the upper pivot 300g. To adjust the space between the upper pivot 300g and the lower pivot 400g, driver grooves 320g and 420g formed in the upper pivot 300g and the lower pivot 400g may be used to rotate each of the pivots 300g and 400g, or a rotary knob 530g provided in the middle region of the connection member 500g may be used to rotate the connection member 500g.

Figure 8D:
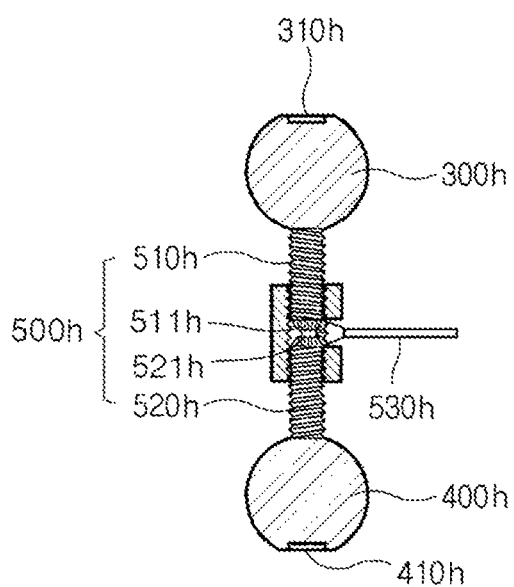

Referring to FIG. 8D, a connection member 500h having adjustment screws 510h and 520h is extended from an upper pivot 300h and a lower pivot 400h like that of FIG. 8B, and adjustable ends 511h and 521h are provided at the ends of the adjustment screws 510h and 520h in the form of a bevel gear. Such a pair of adjustable ends 511h and 521h is engaged with an adjustment member 530h so that the adjustment screws 510h and 520h can get further away from or closer to each other. In this case, a user rotates the adjustment member 530h to adjust a space between the adjustment screws 510h and 520h.

If the adjustment member 530h is pushed in and rotated, the adjustment screws 510h and 520h get further away from each other. On the other hand, if the adjustment member 530h is pulled out and rotated, the adjustment screws 510h and 520h get closer to each other. Alternatively, instead of using the adjustment member 530h, the driver grooves 310h and 410h provided on the ends of the upper pivot 300h and the lower pivot 400h may be used to adjust the space between the adjustment screws 510h and 520h. Thus, the pivots 300h and 400h get closer to or further away from each other while the upper pivot 300h and the lower pivot 400h are respectively bound in the upper teeth supporter 100 and the lower teeth supporter 200.

The adjustable ends 511h and 521h given in the form of the bevel gear have extension shafts extended in a direction perpendicular to a rotary surface, and each of the adjustment screws 510h and 520h has an accommodating hole for accommodating each of the extension shafts. An outer surface of the extension shaft and an inner surface of the accommodating hole are threaded corresponding to each other, so that the extension shaft and the accommodating hole can be screw-coupled to each other. Thus, the adjustment screws 510h and 521h get closer to or further away from each other by rotation of the adjustable ends 511h and 521h.

By the orthopedic appliance with this configuration according to an exemplary embodiment, the temporomandibular joint is corrected by adjusting relative movement in horizontal direction and height between the upper teeth supporter 100 and the lower teeth supporter 200 in accordance with a user's teeth position.

According to an exemplary embodiment, it is easy to adjust relative movement in a horizontal direction and height between the upper and lower teeth supporters.

What is claimed is:

1. An orthopedic appliance for a temporomandibular joint, comprising:
    an upper teeth supporter and a lower teeth supporter, each of which comprises a front arch portion corresponding to front teeth, and a pair of rear legs extended from the front arch portion, the pair of rear legs facing to each other and corresponding to a molar region; and
    at least one set of upper and lower pivots respectively coupled to the upper teeth supporter and the lower teeth supporter to be accommodated in the upper teeth supporter and the lower teeth supporter, said at least one set of upper and lower pivots pivotally rotatable in at least one direction;
    wherein each of the upper and lower pivots includes a vertical inner hole with an engagement screw portion of female threads formed therein,
    wherein the upper and lower pivots of each set of upper and lower pivots are connected to each other by a connection member bridging the upper and lower pivots, the connection member linearly extending in an axial line of the connection member and rotatable with respect to the axial line, and the connection member is formed of a singular body and includes an upper end and a lower end, with an adjustment screw portion of male threads formed on both the upper and lower ends of the connection member,
    wherein the adjustment screw portions on the upper and lower ends of the connection member are spiraled in opposite directions to each other, and the engagement screw portions in the upper and lower pivots are spiraled in opposite directions to each other, and wherein the adjustment screw portions of the upper and lower ends of the connection member are screw coupled to the engagement screw portions of the upper and lower pivots, respectively, such that, when the connection member is rotated with respect to the axial line, a distance between its corresponding upper pivot and lower pivot is adjusted, and thus, enabling to adjust a distance between the upper teeth supporter and the lower teeth supporter.

2. The orthopedic appliance for the temporomandibular joint according to claim 1, wherein at least two sets of upper and lower pivots are coupled to the upper teeth supporter and the lower teeth supporter, including one set in each lateral side of the rear legs.

3. The orthopedic appliance for the temporomandibular joint according to claim 1, wherein each of the upper pivot and the lower pivot of the at least one set of the upper and lower pivots have spherical outer surfaces, and the upper and lower teeth supporters respectively comprise pivot accommodating portions having spherical inner surfaces corresponding to the spherical outer surfaces of the upper and lower pivots and accommodating the upper and lower pivots to be rotatable.

4. The orthopedic appliance for the temporomandibular joint according to claim 1, wherein at least three sets of upper and lower pivots are coupled to the upper teeth supporter and the lower teeth supporter, including one set in each lateral side of the rear legs, and another set in the front arch portions of the upper teeth supporter and the lower teeth supporter.

5. The orthopedic appliance for the temporomandibular joint according to claim 1, wherein at least one or both of the upper and lower ends of the connection member comprises a driver groove for rotation control, and the vertical inner hole of each or at least one of the upper and lower pivots is a through hole to allow insertion of a screw driver therethrough to rotate the connection member.

6. The orthopedic appliance for the temporomandibular joint according to claim 1, wherein at least one of the upper pivot and the lower pivot comprises a stop projection for stopping rotation of the pivot with regard to an axial line, and the rear leg comprises a stopper to engage with the stop projection and for stopping the rotation of the pivot with regard to the axial line.

7. The orthopedic appliance for the temporomandibular joint according to claim 1, wherein the connection member comprises a rotary knob in a middle region thereof for rotation control.

8. The orthopedic appliance for the temporomandibular joint according to claim 1, wherein one set of upper and lower pivots are coupled to the front arch portions of the upper teeth supporter and the lower teeth supporter, and wherein the orthopedic appliance further comprises at least two springs coupled to lateral sides of the rear legs.

* * * * *